United States Patent
Proehl et al.

(10) Patent No.: US 8,259,294 B2
(45) Date of Patent: Sep. 4, 2012

(54) METHOD AND DEVICE FOR MEASURING OPTICAL CHARACTERISTIC VARIABLES OF TRANSPARENT, SCATTERING MEASUREMENT OBJECTS

(75) Inventors: Holger Proehl, Dresden (DE); Thomas Knoth, Dresden (DE); Tina Schoessler, Dresden (DE); Martin Dimer, Dresden (DE)

(73) Assignee: Von Ardenne Anlagentechnik GmbH, Dresden (DE)

( * ) Notice: Subject to any disclaimer, the term of this patent is extended or adjusted under 35 U.S.C. 154(b) by 0 days.

(21) Appl. No.: 13/387,788

(22) PCT Filed: Aug. 11, 2010

(86) PCT No.: PCT/EP2010/061695
§ 371 (c)(1),
(2), (4) Date: Mar. 26, 2012

(87) PCT Pub. No.: WO2011/029685
PCT Pub. Date: Mar. 17, 2011

(65) Prior Publication Data
US 2012/0182545 A1    Jul. 19, 2012

(30) Foreign Application Priority Data
Sep. 9, 2009   (DE) .................. 10 2009 040 642

(51) Int. Cl.
*G01J 1/04* (2006.01)
(52) U.S. Cl. ........................................ 356/236; 356/436
(58) Field of Classification Search .................. 356/236, 356/213–215, 220, 432
See application file for complete search history.

(56) References Cited

U.S. PATENT DOCUMENTS

| | | | |
|---|---|---|---|
| 5,218,417 A | 6/1993 | Gay et al. | |
| 5,764,352 A | 6/1998 | Kappel et al. | |
| 5,923,039 A * | 7/1999 | Jablonski et al. | 250/373 |
| 6,275,295 B1 * | 8/2001 | Sopori | 356/446 |
| 6,424,413 B1 * | 7/2002 | Weber et al. | 356/236 |
| 6,583,879 B1 * | 6/2003 | Berg et al. | 356/402 |
| 2003/0011767 A1 * | 1/2003 | Imura et al. | 356/326 |
| 2003/0202180 A1 * | 10/2003 | Gobel et al. | 356/326 |
| 2010/0188651 A1 * | 7/2010 | Kostuch et al. | 356/73 |

FOREIGN PATENT DOCUMENTS

| | | |
|---|---|---|
| DE | 19628250 A1 | 1/1997 |
| DE | 19528855 A1 | 2/1997 |
| DE | 10010213 A1 | 9/2001 |
| WO | 2008052526 A1 | 5/2008 |
| WO | 2009014866 A1 | 1/2009 |

OTHER PUBLICATIONS

International Search Report for PCT/EP2010/061695 dated Nov. 16, 2010.

* cited by examiner

*Primary Examiner* — Tarifur Chowdhury
*Assistant Examiner* — Michael P Lapage
(74) *Attorney, Agent, or Firm* — Heslin Rothenberg Farley & Mesiti P.C.

(57) ABSTRACT

A method and device are provided for measurement of various transmission and reflection values of transparent measurement objects having transparent layers in an inline coating system, and particularly the turbidity of the measurement object during a relative movement between the measurement object and measuring device. Transmission fractions are measured in two different radiation directions of a lighting source emitting diffuse light by two photodetectors, by which a fraction of diffuse light of the lighting source is suppressed in one direction.

15 Claims, 4 Drawing Sheets

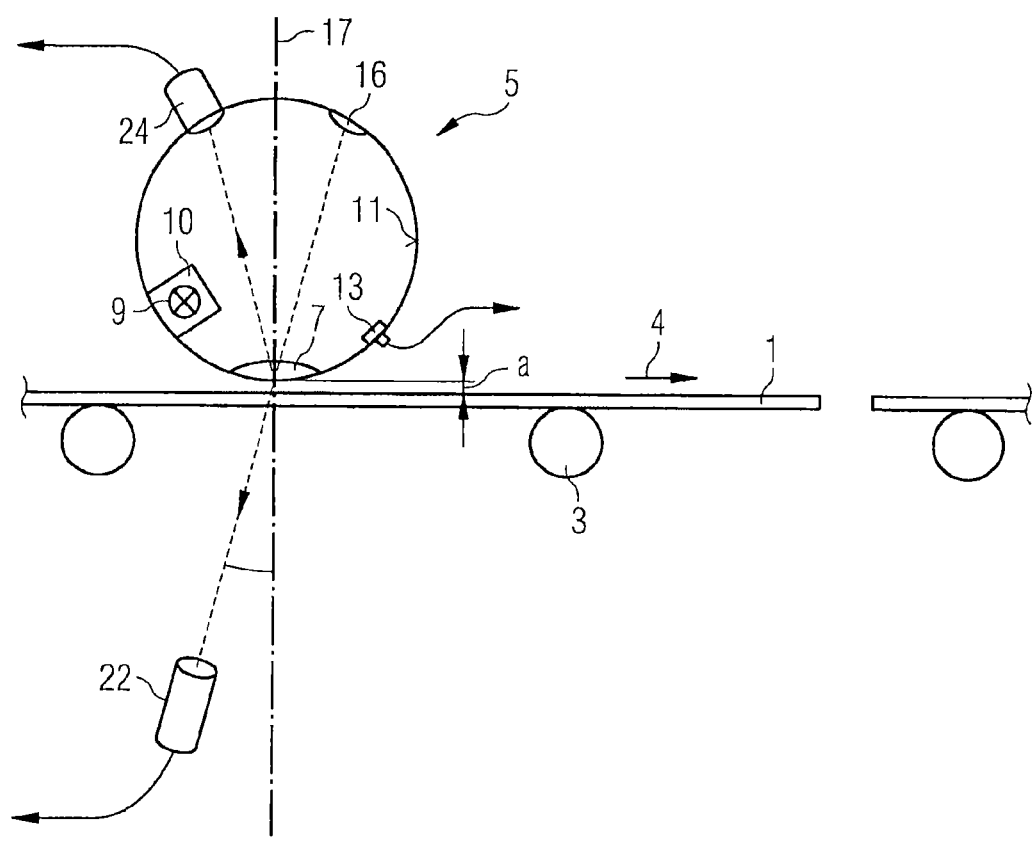

Figure 1:
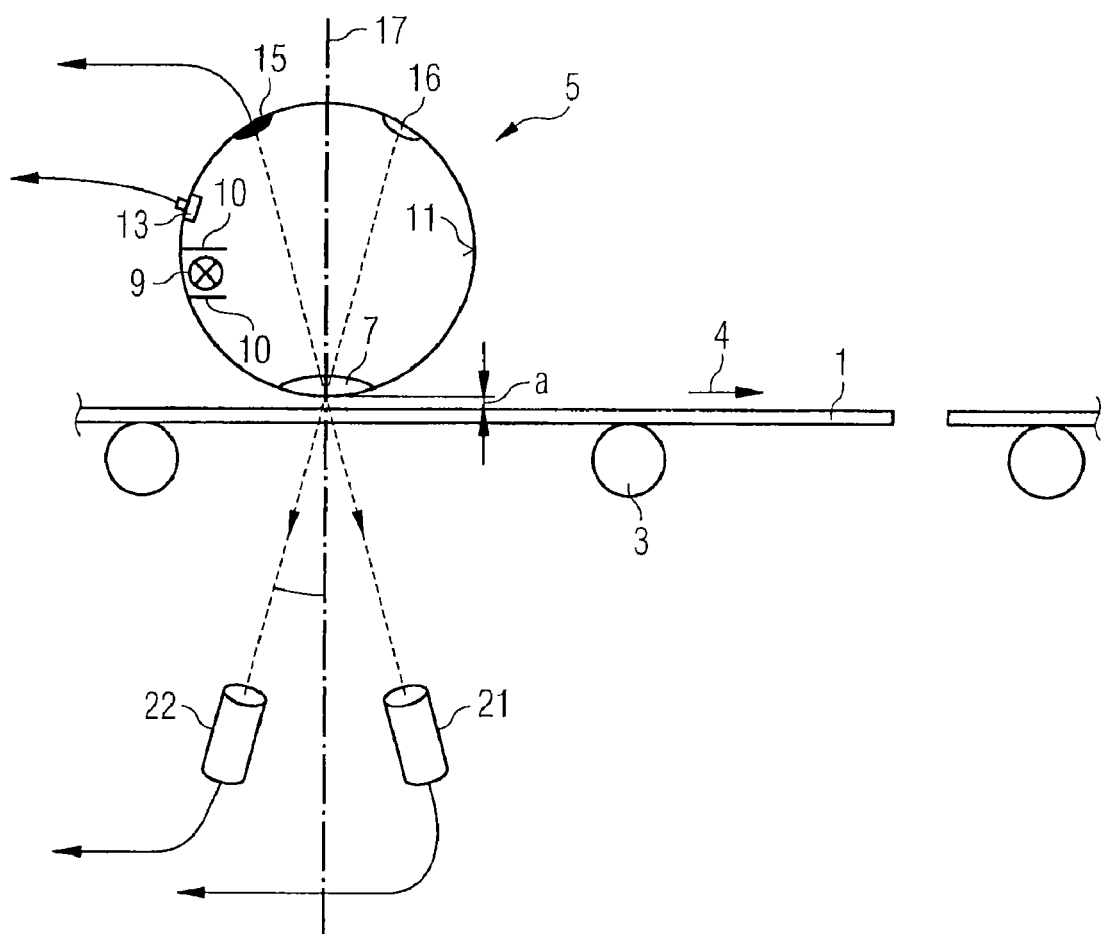

METHOD AND DEVICE FOR MEASURING OPTICAL CHARACTERISTIC VARIABLES OF TRANSPARENT, SCATTERING MEASUREMENT OBJECTS

CROSS REFERENCE TO RELATED APPLICATIONS

This application is a national stage filing under section 371 of International Application No. PCT/EP2010/061695 filed on Aug. 11, 2010, and published in German on Mar. 17, 2011 as WO 2011/029685 A1 and claims priority of German application No. 10 2009 040 642.5 filed on Sep. 9, 2009, the entire disclosure of these applications being hereby incorporated herein by reference.

Background Art

The invention relates generally to a method for measuring optical characteristic variables of transparent, scattering measurement objects and to a device for carrying out the method. It relates in particular to the measurement of various transmission and reflection values of plate- or strip-type substrates that are provided with transparent layers in an inline coating apparatus. The invention likewise relates to a device for carrying out the method.

Optical characteristic variables obtained by reflection and/or transmission measurements are often used for characteristic transparent substrates with or without a coating and likewise for quality assurance in the production of layers and layer systems. On the basis of these characteristic variables, it is possible to draw direct conclusions about properties of the coated substrates which are of interest for the respective purpose of use thereof. Merely by way of example, mention shall be made here of the transmission, reflection, absorption and emission properties, the color values, the layer thickness and the homogeneity thereof.

For electrically conductive layers which, in photovoltaics, for example, are applied as surface contacts on a substrate, the sheet resistance, for example, is to be monitored. If said surface contact is arranged on the light incidence side of the layer stack of a solar cell, the transparent properties are also of importance. For as is known, on the one hand, high light incidence is to be made possible, and, on the other hand, a certain amount of light scattering in the layer is favorable in order to improve the coupling of light into the absorbent semiconductor.

One measurement of the scattering of a layer or of an arbitrary transparent measurement object is the haze thereof, also designated as large-angle scattering. This involves, in accordance with the international standard ASTM D 1003, the percentage proportion of the total light passing through a measurement object which experiences in the measurement object a direction deflection of more than 2.5°, i.e. which is scattered out of the directed beam upon passage through the measurement object. This scattered proportion can be determined by masking out the directed proportion of the transmitted light. The light scattering can be caused not only by the surface roughness of the measurement object but also by material inhomogeneities, statistically incorporated particles or the like which lead to the substantially statistical deflection of the light by different angles.

ASTM D 1003 describes two basic methods for determining the haze of transparent, planar measurement objects. In a so-called HAZE meter, a measurement object is arranged directly and in a flat manner upstream of the light entrance opening of a photometer sphere, also designated as Ulbricht sphere or integration sphere and is illuminated unidirectionally from the opposite side to the Ulbricht sphere. By means of a photodetector in the sphere and so-called gloss or light traps arranged at defined angles relative to the light entrance opening for the purpose of masking out the directed proportion, it is possible to measure the different transmission values of the measurement object which take account of light which, on the one hand, is not scattered or is scattered only at a small angle or, on the other hand, is scattered by the measurement object at a relatively large angle (here >2.5°). The first is the total transmission $T_{total}$, and the second is the diffuse transmission $T_{diffuse}$. Apart from relatively small corrections, the haze is determined from the two values by ratio formation:

$$HAZE = \frac{T_{diffuse}}{T_{total}} \times 100\%$$

In accordance with the specification mentioned, on the basis of measurements without a measurement object it is possible to determine the incident light and to take account of the scattering effects of the sphere on $T_{diffuse}$.

In a second method in ASTM D 1003, the Ulbricht sphere serves as an illumination source for illuminating the planar measurement object arranged directly and in a flat manner upstream of the light exit opening of the sphere with diffuse light. By means of a photodetector arranged on the other side of the measurement object, the transmission values required for the above calculation can once again be measured. The different transmission values can be determined by activating and deactivating the light traps.

While DE 196 28 250 A1 uses the illumination by means of unidirectional light for the measurement of the large-angle scattering, DE 195 28 855 A1 describes the spectral transmission measurement using diffuse illumination of the measurement object. With both methods described, and also in the case of the measurement specification in ASTM D 1003, two measurements that are to be carried out successively are required in order to determine the haze of the transparent measurement object, one measurement for determining the total transmission and one for determining the diffuse transmission. On account of this measurement sequence, however, it is not possible to perform haze measurements in an inline coating apparatus for quality assurance, in which usually planar substrates are coated continuously and in relatively large quantities.

Therefore, the invention addresses the problem of specifying a method for measuring optical characteristic variables of transparent measurement objects and a device for transmission measurement with which the desired characteristic variables and, in particular, the haze of the measurement object can be determined inline, i.e. also during a relative movement between measurement object and measuring device, and can thus be used for the ongoing monitoring of the characteristic variable in an inline apparatus.

Brief Summary of Invention

A measuring method is specified in which two different transmission values, the total transmission and the diffuse transmission, can be measured simultaneously by means of two separate measurement channels, by virtue of separate photodetectors being used for both measurements. For each of the photodetectors, a different proportion of the light passing through the measurement object is selected by means of the illumination source that emits diffuse light being modified in such a way that the directed transmission is masked out in at least one direction, such that no light from the illumination source is directly incident on the photodetector oriented in this direction. This ensures that in this direction only light scattered by the measurement object, i.e. the diffuse transmission $T_{diffuse}$ thereof, is detected. With the second photodetector, which has a different orientation, a proportion of the light which impinges on the photodetector from the illumination source through the measurement object ($T_{total}$) is detected. The haze of the measurement object can be determined from both values, as described above.

Although the light detection, in the two measurement channels should be effected in the same way or if this is not possible, systematic deviations in the measurement on account of the optical elements and detectors used are to be taken into account. These can be determined and/or eliminated by suitable calibration.

The orientation of the photodetectors and thus the definition of the selected radiation directions are effected on the basis of the light exit opening of the illumination source and the measurement axis running through the latter. Various scattering angles can be measured for the measurement, e.g. the angle of 8° as defined by ASTM D 1003, such that the normalized measurement d/8° is realized for the transmission measurement. Other arbitrary angles of the scattering or directed transmission can also be measured, including simultaneously, by means of corresponding detector arrangements.

The simultaneous measurement of the two transmission values $T_{total}$ and $T_{diffuse}$ allow the measurement during a relative movement between measurement object and measuring device. The relative movement can be realized arbitrarily by the measurement object alone, by the measuring device or both together. The measuring method described below can be used to constantly monitor e.g. planar or strip-type substrates on which transparent layers are intended to be applied in an inline coating apparatus and which are transported for this purpose continuously or else discontinuously through the apparatus. Instead of this or simultaneously, the measuring device can be moved over the substrate in order to determine local dependencies e.g. transversely with respect to substrate transport. In this way, measurement points can be placed in a distributed manner in situ, inline and continuously on the measurement object, e.g. along arbitrary measurement tracks running over the measurement object.

Various devices which emit diffuse light and which enable masking-out in one direction can be used as the illumination source. Diffuse light with a relatively uniform distribution of the light virtually in the entire half-space is obtained by using an Ulbricht sphere. An integration or Ulbricht sphere is a hollow sphere having an inner surface having absolutely matt reflection properties. The light of a light source arranged in the interior of the sphere is multiply diffusely reflected, such that every portion of the inner area, thus including a light exit opening, is illuminated with equal intensity and its luminance is proportional to the total luminous flux. Equally, however, it is also possible to use illumination sources which are fashioned in a comparable manner as hollow bodies with a highly reflective and diffusely scattering, i.e. white inner surface and/or which have diffusing screens at the light exit opening for the purpose of scattering light.

When an Ulbricht sphere or a comparable hollow body is used, a directed light proportion can be masked out by means of light traps in the hollow body. Said light traps do not have the highly reflective property and are realized by openings in the hollow body or black diaphragms. The light traps can be activated and deactivated usually in a simple manner by closing or opening the openings or by positioning the diaphragms.

In order to support the possible relative movement between measuring device and measurement objects, in one configuration of the method and of the device used therefor, a distance a can be arranged between the measurement object and the illumination source. A distance that is intended to be greater than zero should be understood to mean that the illumination source, unlike in the measurement specification ASTM D 1003 and in the prior art described above, is not intended to bear directly against the measurement object.

In this case, the distance between the two should be kept as small as possible in order to minimize the influencing of the measurement by the distance. Consequently, the distance is determined by the fact that an unimpeded movement of the two relative to one another is just still possible in an unimpeded manner without illumination source and measurement object touching one another. Such a distance is to be set particularly when large-area substrates are measurement object, in the case of which it is necessary to reckon with warpages, flexures as a result of supports at a distance or fluctuations in the thickness of one or more successive substrates. These fluctuations in height determine the distance a.

A relative movement between the illumination source and the measurement object includes, of course, the movement of the photodetectors and of all further components which are connected to the illumination source or oriented with respect thereto. Consequently, these components and in this case at any rate the two photodetectors of the measuring device are moved jointly, such that the inner geometry of the measuring device is not altered on account of the movement.

For the realization of this joint movement, various concepts are known to the person skilled in the art depending on the shape and the size of the measurement object and on the type of movement. Thus, by means of a continuous, i.e. uninterrupted, relative movement, the measurement object can be scanned, wherein measurement object and measuring device can undergo mutually decoupled, including non-uniform, movement sequences in order to measure the desired area or track on the measurement object.

A finite distance a, and particularly if the latter fluctuates on account of the relative movement, leads to an influencing of the measurement signal of a scattering measurement object, since a finite proportion with a large angle no longer impinges on the measurement object from the illumination source on account of said distance. Moreover, when an Ulbricht sphere or a comparable illumination source is used, an increased light incidence in the sphere can be registered, which corrupts the characteristics of the illumination source. These effects are intensified with increasing scattering and increasing reflection of the measurement object and corrupt both measured transmission values.

In order to know the influence of these effects on the measurements, and if appropriate to take account of that, in one configuration of the invention, a reference measurement of this proportion is effected in the hollow body of the illumination source by means of a reference photodetector arranged there. The latter is arranged in the illumination source in such a way that no light from the light source is incident directly on the photodetector in the hollow body. From the light intensity measured by means of the reference photodetector, the change in intensity of the illumination source that is caused by drifting or effects mentioned above can be determined at any time. The corruption can thereupon be eliminated by suitable calibration methods. Such calibration measurements can also be performed inline in the course of the measurement process, by means of the measuring device being moved to a location at which no measurement object is present, or a measurement being initiated in such an intermediate position. Such a measurement without a measurement object is suitable for at least partly detecting the effects described.

Furthermore, on account of restricted adjustment possibilities, e.g. in an inline apparatus and as a result of inequalities in the beam path, the effects associated with the distance a can be manifested to different degrees for the two measurement channels of the first and second photodetectors.

For this reason, in accordance with one configuration of the measuring method, a calibration measurement comprising at least three measurements is performed. In the context of this calibration measurement, firstly a measurement designated as dark measurement is effected. In this case, intensity measurements are effected by means of a reference photodetector arranged in the illumination source as described above, designated hereinafter as reference channel, and by means of the first and second photodetectors, both designated hereinafter as diffuse and total transmission channels, with the illumination source switched off. These measurement results yield a background proportion of the reference channel and a background proportion of the transmission channels, which are determined by the dark noise of the photodetectors but also by scattered light being coupled in from the environment of the measuring arrangement. A corresponding correction of the measurement results is obtained with the aid of subtraction of these background proportions from the subsequent measurements.

This is followed by a so-called dummy measurement without a sample or on a sample which does not scatter or scatters to a small extent, as represented e.g. by an uncoated plane-parallel glass substrate, the transmission behavior of which is known. Generally, a sample which does not scatter or scatters to a small extent with a haze of less than 0.5% is assumed, where here the term sample was chosen merely for differentiation relative to the measurement object. In principle, a sample is also a measurement object, but usually with known properties.

The dummy measurement is likewise effected by means of the reference channel and the two transmission channels. From the measured values of the reference channel and the channel of total transmission, a proportionality factor is determined, which is a prerequisite for the correct transmission measurement. From the measured values of the reference channel and the channel of diffuse transmission, a calibration measurement is realized, which detects the light proportion scattered into the diffuse transmission channel by the measuring apparatus itself. With the aid of this last-mentioned calibration measurement, the diffuse transmission measurement is to be corrected depending on the transparency of the sample.

This is followed by a so-called scattering measurement on a scattering sample with known transmission and scattering. This scattering measurement is likewise effected by means of the reference channel and the transmission channel of the first photodetector, which measures the diffuse transmission of the sample, and the second transmission channel, which measures the total transmission of the sample. A proportionality factor is determined for both transmission channels, as described above. Said proportionality factor represents light proportions which are driven by the distance between the illumination source and the sample and thus by the absence of light with a large angle of incidence.

For the scattering measurement it is possible to use a sample whose transmission and scattering are in the range of the values to be expected for the measurement object. A good calibration can be obtained in this way. The range respectively to be taken as a basis is to be determined by simple sample measurements or experiments. A purely linear calibration measurement of the measurement channels becomes possible with this factor.

Supplementarily, the non-linearity of the measurement channels can be eliminated by means of a fourth measurement on a further known, scattering sample having transmission and scattering properties deviating from the above-mentioned sample.

By means of the measuring device described, further optical characteristic values of the measurement object which are based on the transmission measurement can be determined in further configurations of the method. Thus, color values can be determined or the measurements can be performed in an angle-dependent manner by means of corresponding orientation of the photodetectors, alternatively also by means of supplementary photodetectors, wherein collimated monochromatic light, preferably laser light, is used for multiple, simultaneous scattering angle measurements. Generally, either monochromatic or polychromatic light can be used for illumination.

Reflection measurements too, can supplementarily be carried out given corresponding configuration of the measuring device with an Ulbricht sphere or a comparable illumination source. With this objective, photodetectors which, in a comparable manner to the transmission measurement, measure the diffuse reflection proportion and the total reflection proportion are arranged in the beam path of the light reflected by the measurement object. In this case, total reflection proportion should be understood to mean that proportion which, in accordance with the total transmission, comprises both the directed reflection and the diffuse reflection in the same direction, by means of the orientation of the photodetector for this measurement in such a beam path which is incident on the measurement object from the diffusely reflective surface, e.g. of an inactive light trap.

Since the light incident on the measurement object originates from a point of the inner surface of the illumination source, the photodetector of the reflection measurement is also to be integrated in the surface. If the total measurement and the diffuse measurement are measured in one measuring arrangement, the two photodetectors thereof are realized in two different measurement planes, which can be e.g. at right angles to one another. With regard to the measuring arrangement, reference is made to the explanations of the exemplary embodiments.

In a manner comparable to the above-described calibration for the transmission measurement, background proportions are also to be determined for the reflection measurement and taken into account in order to obtain corrected reflection values.

Furthermore, in parallel with the transmission measurement, the measurement of the sheet resistance is also possible, wherein, for the case of movement between measuring device and measurement object, a contactless resistance measurement can be effected e.g. by means of a radiofrequency eddy current method. Through a combination of the measuring heads for the transmission measurement and for the resistance measurement, it is possible to monitor the optical characteristic values and the sheet resistance at the same location of the measurement object.

Brief Description of Drawing Figures

Figure 2A:
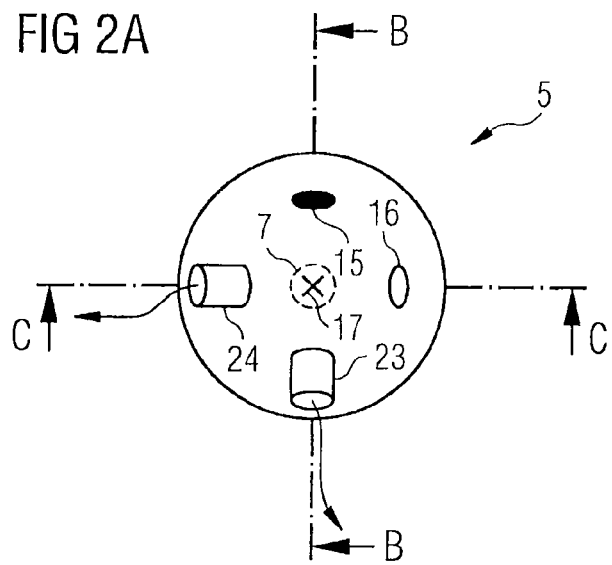
Figure 2B:
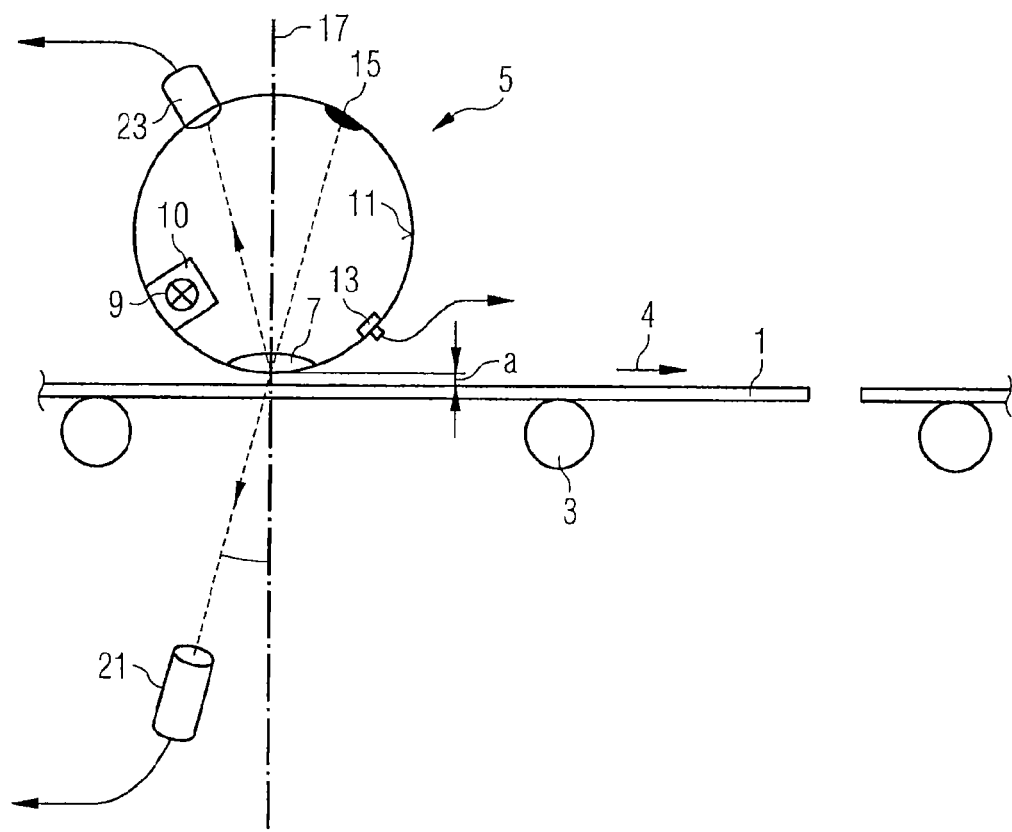
Figure 3:
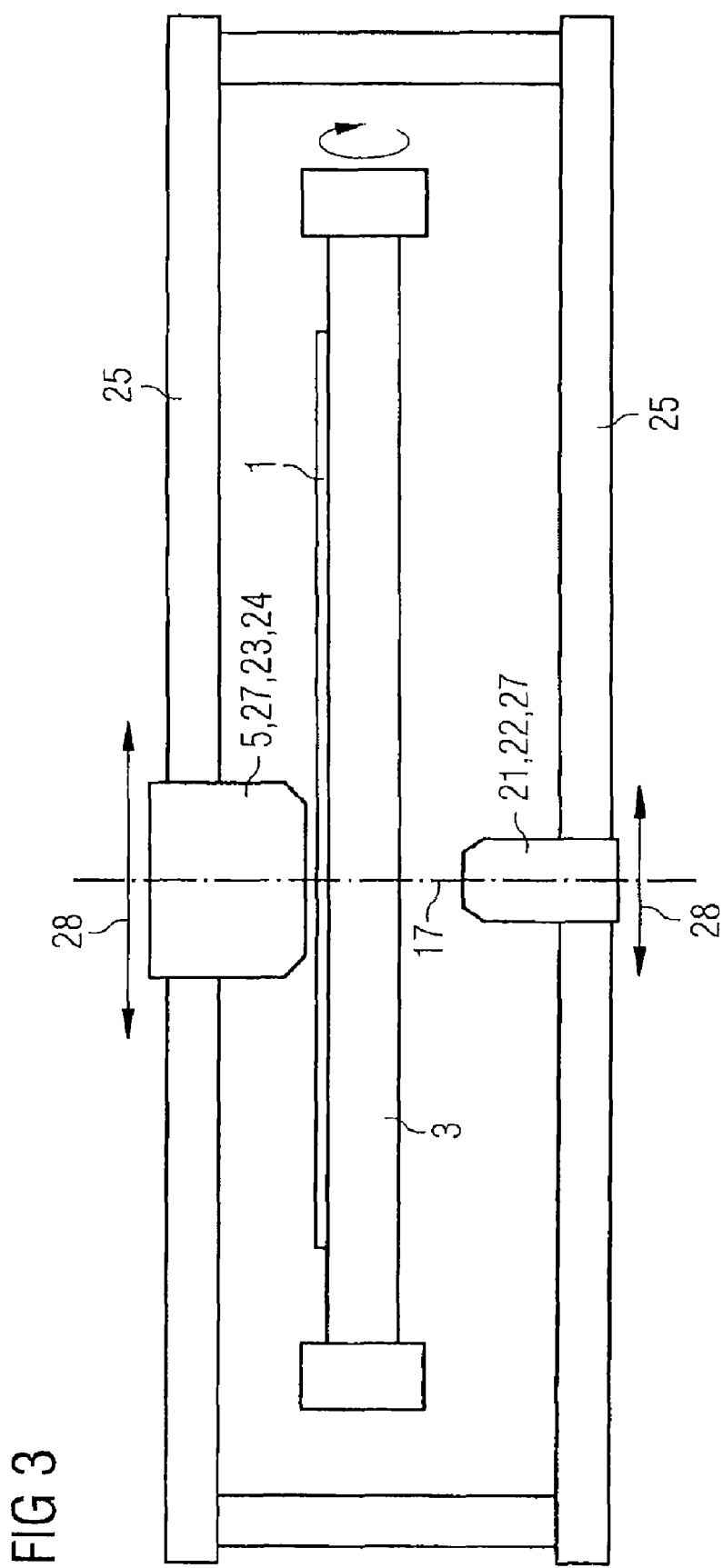

The invention will be explained in greater detail below on the basis of an exemplary embodiment. In the associated drawing:

FIG. 1 shows a schematic construction of a measuring device for measuring total and diffuse transmission on a moved plate-type measurement object, FIG. 2A shows a schematic construction of a measuring device for measuring the diffuse and total transmission and the diffuse and directed reflection in plan view, FIG. 2B shows a schematic construction of a measuring device according to FIG. 2A along the sectional line B-B for measuring the diffuse proportion of transmission and reflection, FIG. 2C shows a schematic construction of a measuring device according to FIG. 2A along the sectional line C-C for measuring the proportions of the total transmission and directed reflection, and FIG. 3 shows a schematic illustration of a movable measuring device in accordance with FIG. 1.

DETAILED DESCRIPTION

The measuring device in accordance with FIG. 1 comprises an illumination source 5, in the illustrated exemplary embodiment an Ulbricht sphere, which is arranged above a flat, plate-type and measurement object 1, designated generally and thus also hereinafter as substrate 1. The substrate 1 is transparent and has a transparent and scattering coating. A sequence of substrates 1 is illustrated, which is moved by means of a transport device 3 in a substrate transport direction 4 continuously or discontinuously through a coating apparatus (not illustrated). In the coating apparatus, a transparent electrically conductive layer is continuously applied on the sequence of substrates and subjected to after treatment e.g. by means of a suitable etching method for producing the light-scattering property. The haze of the coated substrate is intended to be measured constantly and in a distributed manner on the substrate by means of the measuring device illustrated. Alternatively, other transparent and scattering measurement objects can also be measured.

The illumination source 5 has, opposite the substrate 1, a light exit opening 7 and is arranged with the latter at a distance a above the substrate 1. In the case of the illustrated large-area substrates 1 such as are coated for photovoltaics, the distance a is in the range of between 1 and 10 mm. Other distances a may be necessary in the case of other measurement objects 1.

A light source 9 adapted to the desired spectrum, e.g. a halogen lamp, is arranged in the illumination source 5. The light from the light source 9 is multiply reflected by the highly reflective and diffusely scattering inner surface 11, such that from the light exit opening 7 diffuse light is incident on the substrate 1.

The light source 9 is shielded by suitable diaphragms 10 such that no direct light reflection impinges on the light exit opening 7, and equally little on a reference photo sensor 13, in the sense of a measurement channel also designated as reference channel 13, which is likewise arranged in the interior of the illumination source 5.

The illumination source 5 furthermore comprises two light traps 15, 16, in the exemplary embodiment holes in the wall of the sphere, which are to be opened and closed again and are active in the opened state, that is to say that light impinging on the active light trap 15 in this state leaves the illumination source 5 through the opening (represented by a dotted line), such that no light is reflected from this location of the inner surface 11 of the illumination source. In the inactive state, this part of the inner surface 11 has the same reflection properties as the rest of the inner surface 11. It is designated hereinafter as inactive light trap 16 for clarification purposes. In the figures, an active light trap 15 is represented by a black area, and an inactive light trap 16 by a white, bordered area.

In the exemplary embodiment illustrated, the illumination source 5 has two light traps 15 and 16, of which one is active and one is inactive. Further light traps 15 and 16 or installations in the illumination source 5 are possible for various of the measurements described above, but are not illustrated here for the sake of better clarity. In principle, however, only one active light trap 15 is necessary for the haze measurement described above.

The two light traps 15, 16 in FIG. 1 are arranged symmetrically with respect to the optical axis 17 of the illumination source 5, which simultaneously forms the measurement axis in the exemplary embodiment. The light traps 15, 16 are arranged in such a way that a straight line through the center of the light exit opening 7 to the center of the respective light traps 15, 16 (represented by a dashed line) forms an angle of 8° with the optical axis 17, such that the standard measurement geometry d/8° can be realized. Alternatively or supplementarily, other angles can also be set, as long as, for the measurement of the wide-angle scattering which is required for determining the haze, at least one such wide angle is realized.

Two photodetectors 21, 22 are arranged on the opposite side of the substrate 1 to the illumination source 5. All types of photoelectric components which are designed for the spectrum used, such as e.g. various photocells or phototransistors, can be used as photodetectors 21, 22. Preference is given to photoelectric components that are sensitive over the entire wavelength range of visible light. More complex optical systems, which comprise e.g. a spectral resolution, can also be employed as a photodetector. By way of example, collimating optical units, optical waveguides, spectrometers or the like can be used.

The two photodetectors 21, 22 are arranged symmetrically with respect to the measurement axis 17 of the measuring system in such a way that each of them is oriented toward a different one of the two light traps 15, 16. Since one of the light traps 15 is active, by means of the photodetector 21 oriented toward it, designated hereinafter as first photodetector 21 or diffuse transmission channel 21, the diffuse transmission $T_{diffuse}$ of the light that is emitted by the illumination source 5 and passes through the substrate 1 is measured. The second photodetector 22, which has an orientation deviating from the first photodetector 21, and which is oriented towards the second, inactive light trap 16 in the exemplary embodiment, serves for measuring the total transmission $T_{total}$. For differentiation purposes, the second photodetector 22 is also designated as total transmission channel 22. Since the total transmission channel 22, for this purpose, has to look at a section of the diffusely reflective inner surface 11, it can alternatively also have a different orientation, the standard measurement geometry d/8° no longer being realized in this case.

By means of the measured values of the two transmission channels 21, 22 and of the reference channel 13, the haze of the coated substrate 1 is to be determined taking account of the corrupting light proportion backscattered into the illumination source 5, as described in detail above and as can also be gathered from ASTM D 1003. The current measurement point of the measurement object 1 is always the point coinciding with the measurement axis 17. An exact spatial assignment of a multiplicity of successively measured measurement points is possible by way of the known movement sequence of the substrate 1. Alternatively, a measurement is also possible when the substrate is at a standstill. A measurement without a measurement object 1 for calibration purposes can be effected in the exemplary embodiment e.g. whenever there is a gap in the sequence of substrates 1 below the light exit opening 7.

FIGS. 2A to 2C illustrate an embodiment variant of the measuring device by means of which the proportion of the directed reflection and of the diffuse reflection of the measurement object can be measured simultaneously.

The plan view in FIG. 2A of an Ulbricht sphere as an illumination source 5 of the measuring device illustrates an active light trap 15, which, of course, is active on the inner surface 11 of the illumination source 5 and is illustrated here merely in terms of its position. The photodetectors for the measurement of the diffuse proportions of reflection and transmission are arranged in the same measurement plane in which the sectional line B-B was placed in FIG. 2A, wherein only the third photodetector 23, designated as diffuse reflection channel 23, can be seen since the first photodetector 21, i.e. the diffuse transmission channel 21, is situated below the illumination source 5 and is therefore not visible in FIG. 2A.

In the measurement plane which is at right angles to that of the diffuse reflection and transmission measurement and coincides with the sectional line A-A in FIG. 2A, an inactive light trap 16 is illustrated schematically on the outer surface of the illumination source 5. In this measurement plane, the second photodetector 22 or the total transmission channel 22 (not visible since below the illumination source 5) and the fourth photodetector 24 are arranged. The latter measures the directed reflection of the light proportion that is incident on the substrate from the inactive light trap 16 and is therefore also designated hereafter as directed reflection channel 24.

Both reflection channels 23, 24 respectively lie symmetrically opposite the corresponding light trap 15, 16, relative to the measurement axis 17 of the measuring device, which runs centrally through the light exit opening 7 of the illumination source 5. In FIG. 2A, the measurement axis 17 is perpendicular to the plane of the drawing and is therefore merely illustrated as a cross.

The measurement plane of the diffuse reflection and transmission measurement, in accordance with FIG. 2A the plane along the sectional line B-B, is illustrated in FIG. 2B. With the aid of the dashed line, it is possible to follow the beam path through the substrate 1 to the diffuse transmission channel 21 and reflected at the substrate 1 to the diffuse reflection channel 23. By virtue of the position of the active light trap 15, the standard measurement geometry d/8° is again realized here, too.

Here, too, the light source 9 is once again mounted, by virtue of diaphragms 8, in such a way that no direct light passes through the light exit opening 7, into the reference channel 13 or the diffuse reflection channel 23. With regard to the further configuration of the measuring device, in particular with respect to the illumination source 5 or the spatial relation of the measuring device with respect to the substrate 1, reference is made to the above explanations concerning FIG. 1.

FIG. 2C illustrates the same measuring device as FIG. 2A and FIG. 2B, but in the sectional plane C-C from FIG. 2A. This sectional plane corresponds to the plane for measuring the total transmission and directed reflection. For this purpose, in this plane analogously to the measurement channels in FIG. 2B, once again with the standard geometry d/8°, the total transmission channel 22 is arranged below the substrate 1 and the directed reflection channel 24 is arranged in the Ulbricht sphere of the illumination source 5. The light trap 16 as a starting point for the light proportion detected in these two channels is inactive for this purpose. For the rest, reference is made to the explanations concerning FIG. 1, FIG. 2A and FIG. 2B.

FIG. 3 illustrates an arrangement of the illumination source 5, if appropriate also with the reflection channels 23, 24 and the transmission channels 21, 22 on cross-members 25, which serve for positioning illumination source 5 and transmission channels 21, 22 whilst maintaining their geometrical assignment and orientation with respect to one another over every point of the width of the substrate 1. For the purpose of movement, the illumination source 5 and the transmission channels 21, 22 are mounted on slides 27 which, coupled to one another, can be displaced along the cross-members 25. The illumination source 5 with the associated slide 27 and likewise the transmission channels 21, 22 with their associated slide 27 are illustrated as a compact component in FIG. 2 for the sake of better clarity. The possible slide movement directions 28 are shown by the associated arrows.

In combination with a movement of the substrates 1 along their substrate transport direction 4 (FIG. 1), which in FIG. 2 are perpendicular to the plane of the drawing and thus to the slide movement directions 28, various relative movements and measurement point distributions ensuing therefrom on the substrate 1 are permitted. If the substrate 1 is stationary and only the slides 27 are moved, then measurement points can be set in a manner distributed over the substrate width. If the slides 27 or alternatively the illumination source 5 and the transmission channels 21, 22 without slides 27 are stationary and only the substrate 1 is moved, the measurement track runs parallel to the substrate transport direction 4. If both partners are movable, arbitrary, in the simplest case Z-shaped, measurement tracks can be traversed, such that, depending on the possible speeds, it is possible to effect more or less dense scanning of the substrate 1 for the purpose of monitoring the optical characteristic variables and, by means of suitable (not illustrated in greater detail) evaluation and regulating units (not illustrated), the influencing of the previous coating process.

The invention claimed is:

1. A method for measuring optical parameters of transparent, scattering measurement objects, comprising the following method steps:

illuminating a transparent, scattering measurement object with diffuse light by an illumination source having a light exit opening, wherein a component of the diffuse light in a radiation direction directed from the light exit opening onto the measurement object is suppressed, wherein a integrating sphere having a highly reflective and diffusely scattering inner surface is used as the illumination source, having a light source arranged in an interior of the integrating sphere and a light exit opening apart from said light source, such that no light from the light source passes directly through the light exit opening, and wherein said light proportion in one radiation direction is suppressed by an active light trap arranged in the inner surface of the integrating sphere, detecting light from the illumination source that has passed through the measurement object by two photodetectors directed toward the light exit opening from directions deviating from one another, wherein the photodetectors detect simultaneously, said light trap having a position and direction such that in the direction of one of the two photodectors no light component emerges from the light exit opening, determining diffuse transmission $T_{\mathit{diffuse}}$ of the measurement object from a ratio of light intensity of the light scattered in the measurement object and detected by the first photodetector and the known light intensity of the light incident on the measurement object, and determining the total transmission $T_{total}$ of the measurement object from a ratio of light intensity of light that has passed through the measurement object and been detected by a second photodetector of a total transmission channel, of the photodetectors and the known light intensity of the light incident from the measurement object.

2. The method for measuring optical parameters of transparent, scattering measurement objects as claimed in claim 1, wherein turbidity of the measurement object is determined from the total transmission and diffuse transmission determined.

3. The method for measuring optical parameters of transparent, scattering measurement objects as claimed in claim 2, wherein a light component which arises as a result of straylight incidence or reflections from the measurement object is determined in the integrating sphere by a reference measurement by a reference photodetector of a reference channel arranged in the integrating sphere.

4. The method for measuring optical parameters of transparent, scattering measurement objects as claimed in claim 3, wherein the measuring device is calibrated by carrying out a dark measurement by the reference photodetector arranged in the illumination source and by the first or second photodetector with the illumination source switched off, for the purpose of determining a background component of the reference channel and a background component of the transmission channels, carrying out a dummy measurement without a sample or on a sample that exhibits little scattering by the reference channel and both transmission channels, for the purpose of determining a first proportionality factor, which represents a light component backscattered from the sample into the reference channel, by forming a ratio between the measured value of the reference channel and the measured value of the total transmission channel, for the purpose of determining a second proportionality factor, which represents a light component backscattered from the measuring apparatus into the diffuse transmission channel, by forming a ratio of the measured value of the reference channel and the measured value of the diffuse transmission channel, and carrying out a scattering measurement on a scattering sample having known transmission and scattering by the reference channel and the diffuse transmission channel, which measures the diffuse transmission of the sample, and the total transmission channel which measures the total transmission of the sample, for the purpose of determining a respective proportionality factor for each transmission channel, which represents light proportions given by a distance between the illumination source and the sample.

5. The method for measuring optical parameters of transparent, scattering measurement objects as claimed in claim 1, wherein a component of the light from the illumination source diffusely reflected by the measurement object is detected by a third photodetector of a diffuse reflection channel, being directed within the integrating sphere in that radiation direction which is reflected by the measurement object and in which said component of the diffuse light is suppressed, diffuse reflection $R_{diffuse}$ of the measurement object is determined from a ratio of light intensity of light diffusely reflected at the measurement object and detected by the third detector of the diffuse reflection channel, and the known light intensity of the light incident on the measurement object.

6. The method for measuring optical parameters of transparent, scattering measurement objects as claimed in claim 1, wherein a component of the light from the illumination source directly reflected by the measurement object is detected by a fourth photodetector of a directed reflection channel, being directed within the integrating sphere in a radiation direction which is reflected by the measurement object and in which the diffusely scattered light from the illumination source is incident on the measurement object, and directed reflection $R_{dir}$ of the measurement object is determined from a ratio of light intensity of light directly reflected at the measurement object and detected by the fourth detector of the directed reflection channel, and the known light intensity of the light incident on the measurement object.

7. The method for measuring optical parameters of transparent, scattering measurement objects as claimed in claim 1, wherein the illumination source is arranged at a distance a>0 from the measurement object such that an unimpeded relative movement between the measurement object and the illumination source is just still possible.

8. The method for measuring optical parameters of transparent, scattering measurement objects as claimed in claim 7, wherein a plurality of measurements are carried out at different locations of the measurement object by the illumination source and the detectors being moved jointly and the measurement object being moved relative thereto.

9. The method for measuring optical parameters of transparent, scattering measurement objects, as claimed in claim 8, wherein a calibration of the measuring device is effected, in which diffuse and directed reflection channels and measured values thereof are used instead of the diffuse and total transmission channel and the measured values thereof.

10. A device for measuring optical parameters of transparent, scattering measurement objects, comprising the following components:

an illumination source having a light exit opening for illuminating a measurement object with diffuse light, two photodetectors, which lie in the direction of exiting diffuse light from the light exit at a distance from the light exit opening of the illumination source, wherein each detector input is directed at the light exit opening from direction deviating from one another, wherein the photodetectors detect simultaneously, wherein the illumination source is formed by a integrating sphere having a highly reflective and diffusely scattering, inner surface, a light source arranged in an interior of the integrating sphere and the light exit opening spaced apart from said light source, such that no light from the light source passes directly through the light exit opening, where an inner surface of the integrating sphere has an active light trap in a position and direction such that in the direction of one of the two photodetecters no light component emerges from the light exit opening, a sample accommodating space arranged between the light exit opening of the illumination source and the photodetectors in such a way that light emerging from the illumination source firstly passes through a measurement object arranged within the sample accommodating space and then enters the photodetectors.

11. The device for measuring optical parameters of transparent, scattering measurement objects as claimed in claim 10, comprising the following further components:
  a third photodetector of a diffuse reflection channel arranged in the interior of the integrating sphere symmetrically with respect to the active light trap relative to an optical axis of the integrating sphere as axis of symmetry running through a midpoint of said integrating sphere and a center of the light exit opening,
  wherein no light from the light source is incident directly on the third photodetector.

12. The device for measuring optical parameters of transparent, scattering measurement objects as claimed in claim 10, comprising the following further components:
  a fourth photodetector arranged in the interior of the integrating sphere in a manner deviating from a position which lies symmetrically with respect to the active light trap, relative to an optical axis of the integrating sphere as axis of symmetry running through a midpoint of said integrating sphere and a center of the light exit opening, wherein no light from the light source is incident directly on the fourth photodetector.

13. The device for measuring optical parameters of transparent, scattering measurement objects as claimed in claim 10, wherein a measurement object is positioned in the sample space at a distance from the light exit opening.

14. The device for measuring optical parameters of transparent, scattering measurement objects as claimed in claim 10, wherein the illumination source and the photodetectors are adapted to be moved jointly by a movement device relative to the sample accommodating space.

15. The device for measuring optical parameters of transparent, scattering measurement objects as claimed in claim 10, wherein the device comprises a measuring unit for contactlessly measuring a sheet resistance of the measurement object.

* * * * *